(12) United States Patent
Ebert et al.

(10) Patent No.: US 7,321,427 B2
(45) Date of Patent: *Jan. 22, 2008

(54) MULTIPLE BEAM ELLIPSOMETER

(75) Inventors: Martin Ebert, Fremont, CA (US); Li Chen, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/545,434

(22) Filed: Oct. 10, 2006

(65) Prior Publication Data

US 2007/0030485 A1    Feb. 8, 2007

Related U.S. Application Data

(63) Continuation of application No. 11/256,841, filed on Oct. 24, 2005, now Pat. No. 7,136,164, which is a continuation of application No. 10/893,449, filed on Jul. 16, 2004, now Pat. No. 6,985,228, which is a continuation of application No. 10/042,592, filed on Jan. 9, 2002, now Pat. No. 6,798,512.

(60) Provisional application No. 60/336,437, filed on Nov. 1, 2001, provisional application No. 60/311,035, filed on Aug. 9, 2001.

(51) Int. Cl.
*G01J 4/00* (2006.01)

(52) U.S. Cl. .................. 356/369; 356/368; 356/364

(58) Field of Classification Search ........ 356/364–369, 356/237.1–237; 250/225
See application file for complete search history.

(56) References Cited

U.S. PATENT DOCUMENTS

| 4,585,348 A | 4/1986 | Chastang et al. ........... 356/369 |
| 4,653,924 A | 3/1987 | Itonaga et al. ............. 356/369 |
| 5,091,320 A | 2/1992 | Aspnes et al. ................ 427/8 |
| 5,608,526 A | 3/1997 | Piwonka-Corle et al. ... 356/369 |
| 5,867,276 A | 2/1999 | McNeil et al. .............. 356/445 |

(Continued)

FOREIGN PATENT DOCUMENTS

DE    42 19 691    6/1992

(Continued)

OTHER PUBLICATIONS

N. Blayo et al., "Ultraviolet-visible ellipsometry for process control during the etching of submicrometer features," *J. Opt. Soc. AM. A*, vol. 12, No. 3, Mar. 1995, pp. 591-599.

(Continued)

*Primary Examiner*—Layla G. Lauchman
(74) *Attorney, Agent, or Firm*—Stallman & Pollock LLP

(57) ABSTRACT

An ellipsometric apparatus provides two impinging focused probe beams directed to reflect off the sample along two mutually distinct and preferably substantially perpendicular directions. A rotating stage rotates sections of the wafer into the travel area defined by two linear axes of two perpendicularly oriented linear stages. As a result, an entire wafer is accessed for measurement with the linear stages having a travel range of only half the wafer diameter. The reduced linear travel results in a small travel envelope occupied by the wafer and, consequently, a small footprint of the apparatus. The use of two perpendicularly directed probe beams permits measurement of periodic structures along a preferred direction while permitting the use of a reduced motion stage.

10 Claims, 14 Drawing Sheets

U.S. PATENT DOCUMENTS

| | | | |
|---|---|---|---|
| 5,872,630 A | 2/1999 | Johs et al. | 356/369 |
| 5,963,329 A | 10/1999 | Conrad et al. | 356/372 |
| 5,973,787 A | 10/1999 | Aspnes et al. | 356/369 |
| 5,995,226 A | 11/1999 | Abe et al. | 356/369 |
| 6,031,614 A | 2/2000 | Michaelis et al. | 356/369 |
| 6,134,011 A | 10/2000 | Klein et al. | 356/369 |
| 6,181,421 B1 | 1/2001 | Aspnes et al. | 356/369 |
| 6,256,097 B1 | 7/2001 | Wagner | 356/369 |
| 6,278,519 B1 | 8/2001 | Rosencwaig et al. | 356/369 |
| 6,373,871 B1 | 4/2002 | Hemmes et al. | 372/28 |
| 6,515,745 B2 | 2/2003 | Vurens et al. | 356/369 |
| 6,757,056 B1 | 6/2004 | Meeks et al. | 356/73 |

FOREIGN PATENT DOCUMENTS

| | | |
|---|---|---|
| EP | 62069151 | 3/1987 |
| EP | 04127004 | 4/1992 |
| EP | 0 816 926 | 1/1998 |
| EP | 1 245 922 | 10/2002 |
| JP | 62-28606 | 2/1987 |
| JP | 4-127004 | 4/1992 |

OTHER PUBLICATIONS

K. Hoshi et al., "KrF Resist Pattern Monitoring by Ellipsometry," *Jpn. J. Appl. Phys.*, vol. 36 (1997), pp. 7717-7719.

L-Y. Chen et al., "Improved rotating analyser-polarizer type of scanning ellipsometer," *Thin Solid Films*, vol. 234 (1993), pp. 385-389.

Chen et al., "Design of a scanning ellipsometer by synchronous rotation of the polarizer and analyzer," *Appl. Opt.* vol. 33, No. 7, Mar. 1, 1994, pp. 1299-1305.

J. Lee et al., "Rotating-compensator multichannel ellipsometry for characterization of the evolution of nonuniformities in diamond thin-film growth," *Applied Physics Letters.*. vol. 72, No. 8, Feb. 23, 1998, pp. 900-9002.

J. Lee et al., "Rotating-compensator multichannel ellipsometry: applications for real time Stokes vector spectroscopy of thin film growth," *Review of Scientific Instruments*, vol. 69, No. 4, Apr. 1998, pp. 1800-1804.

US 7,321,427 B2

MULTIPLE BEAM ELLIPSOMETER

CLAIM OF PRIORITY

The present application is a continuation of U.S. patent application Ser. No. 11/256,841, filed Oct. 24, 2005, now U.S. Pat. No. 7,136,164, which is a continuation of U.S. patent application Ser. No. 10/893,449, filed Jul. 16, 2004, now U.S. Pat. No. 6,985,228, which is a continuation of U.S. patent application Ser. No. 10/042,592, filed Jan. 9, 2002, now U.S. Pat. No. 6,798,512. This application claims priority to U.S. Provisional Patent Applications Ser. No. 60/311,035, filed Aug. 9, 2001, and Ser. No. 60/336,437, filed, Nov. 1, 2001, each of which is hereby incorporated herein by reference.

TECHNICAL FIELD OF THE INVENTION

The present invention relates to ellipsometric systems for measuring feature configurations on wafers. Particularly, the present invention relates to a compact ellipsometer having multiple measurement beams. The measurement beams operate alternately and in conjunction with a rotating stage such that linear stages for positioning the wafer may be operated within reduced travel ranges.

BACKGROUND

Semiconductors are typically fabricated by depositing and etching a number of layers that are shaped and configured on the upper or top surface of a wafer. Controlling those fabrication steps and testing the wafer early during production helps to keep production costs low. An increasingly important technique for a non-destructive measurement of semiconductors is ellipsometry. In ellipsometry, a specifically configured probe light beam is directed to reflect off the wafer. The change in polarization state of the beam induced by the interaction with the wafer is monitored to provide information about the wafer.

Ellipsometers have been used extensively to monitor thin film parameters such as thickness, index of refraction and extinction coefficient. More recently, ellipsometers Ellipsometers have been used extensively to monitor thin film parameters such as thickness, index of refraction and extinction coefficient. More recently, ellipsometers have been used to monitor the properties (critical dimensions) of small, repeating, periodic structures on wafers. These periodic structures are similar to a grating and the measured data can be subjected to a scatterometry analysis to derive information about the structure. Information of interest includes, but is not limited to, line width and spacing as well as sidewall profile.

Such periodic structures have distinct orientations. It has been found that the most useful information about such structures can be obtained if the probe beam of the ellipsometer is directed substantially perpendicular to the line structure.

As seen in FIG. 1, a typical wafer W will have multiple such periodic structures PS formed thereon. In some cases, all of the periodic structures will be oriented in the same direction (i.e. all lines parallel). In other cases, some of the structures will have lines running perpendicular to other structures.

A conventional, ellipsometer is typically provided with a stage for moving the wafer through full linear motions FX, FY as well as rotation about the central axis so that the probe beam PB can be directed to each of the periodic structures PS in the appropriate direction (usually perpendicular to the line structure). The linear motions FX, FY are about equal to the wafer diameter WD. The wafer W moved during the measurement consequently occupies a travel envelope LE that extends in the directions of each of the linear axes about twice the wafer diameter. The travel envelope LE determines the minimal footprint of an ellipsometer apparatus.

Recently, there has been a push to substantially reduce the size of ellipsometer apparatus. This effort is particularly directed to allowing an ellipsometer to be incorporated directly into a semiconductor processing tool. To achieve the desired miniaturization, stage system have been developed which reduce the total range of motion of the wafer, thereby reducing the travel envelope and consequently the footprint of the system (e.g. stages that implement a cylindrical coordinate system consisting of a linear and a rotational stage). The use of these stages has not significantly impeded the measurement of thin film parameters since such measurements are not effected by the direction in which the probe beam strikes the sample. However, such reduced motion stage systems have caused a problem with measuring periodic structures where the impinging direction of the probe beam PB has to correspond to a measurement relevant orientation of the periodic structure PS.

As shown in FIGS. 2A and 2B the wafer can be manipulated with the X- and Y-stages such that only one of the four quadrants of the sample is located at the intersection between the sample and the probing beam. To perform measurements within the other three quadrants of the sample, the rotating stage needs to move by multiples of 90°. To achieve perpendicular orientation of the periodic sample structures in these cases, a second probing beam perpendicular to the first one is necessary.

This difficulty can best be seen in FIGS. 2A and 2B. In FIG. 2A, the probe beam PB is shown striking periodic structure PSI perpendicular to the line structure. When the operator wishes to measure periodic structure PS2, the rotating stage is used to bring the sector of the wafer where that structure is located within the region which can be reached by the probe beam. As noted above, the stage travel in the X and Y directions is not sufficient to bring the structure PS2 under the probe beam without a rotation. Unfortunately, and as seen in FIG. 2B, the result of this rotation is to orient the periodic structure PS2 so that the probe beam impinges thereon in a direction parallel to the lines. As noted above, it has been found that most relevant information can be obtained when the beam strikes the structure perpendicular to the line structure.

Accordingly, it would be desirable to develop an ellipsometer system, which can utilize a reduced motion stage but also provides for optimal measurement of both thin film parameters and periodic structures.

BRIEF SUMMARY

In the present invention, a probe beam is selectively directed along two or more beam paths to provide two or more focused beams impinging in various impinging directions on a tested wafer. Two perpendicularly operating linear stages provide a travel area that is only a fraction of the wafer size. Combined with the linear stages is a rotating stage positioned with its axis of rotation perpendicular to the movement plane defined by the linear stages. The movement plane is preferably parallel to the top of the fixed wafer. The rotating stage rotates the fixed wafer within a rotation range such that a number of sectors of the wafer top are brought within range of the respective focal spot during consecutive sector measurement steps. During a sector measurement step, only the linear stages are operated to move the wafer along the focal spot.

The focused beams are positioned in a number and in an angular orientation to each other that corresponds to the number of angular orientations of patterns within the measurement sectors. In the preferred embodiment, where wafer patterns have one measurement relevant orientation, two focused beams are provided in perpendicular impinging directions relative to each other such that the pattern can be measured in all four quadrants while still maintaining a perpendicular orientation of the pattern relative to the plane of the probing beam. Since two focused beams are utilized, the rotating stage operates only to adjust the wafers global orientation prior to the sector measurement steps and to rotate the predetermined sectors within the travel area so that is accessible by the focal spots. In the preferred embodiment, four sectors are defined for measuring a wafer in four consecutive sector measurement steps. The linear ranges of the linear stages are about half the wafer diameter, which significantly reduces the travel envelope and consequently the footprint of the apparatus.

The goal of the subject invention could be achieved using two completely separate ellipsometers mounted on the same support system. In other words, two light sources, two sets of focusing and collecting optics, two sets of polarizers and analyzers and two separate detectors could be used. However, in the preferred embodiment, only a single light source and a single detector are used. This approach not only conserves space, but also reduces complexity as only one light source and one detector needs to be adjusted and characterized for the measurement.

Preferably, a broad band light source is used to generate a polychromatic probe beam. At some point before striking the sample, optics are provided for either splitting the beam along two paths or selectively directing the beam along a first or a second beam path. After reflection off the sample, optics are provided before the detector to either recombine the previously split beam portions or selectively combine the two beam paths into a single path. In the preferred embodiment, movable mirrors are used to create two beam paths rather than splitting the beam to maximize the light energy being used for the measurement.

The subject invention is not limited to any particular ellipsometer configuration. Those skilled in the art will be aware of many variants such as rotating polarizer (analyzer) or rotating compensator systems. The elements necessary to create the polarization state of the incoming probe beam and analyze the polarization state of the reflected beam can be located in the common path regions or in the separate path regions. If located in the separate path regions, two sets of optical elements are needed as shown in the preferred embodiment illustrated herein.

In the illustrated embodiment, a broadband rotating compensator (waveplate retarder) system is shown. Such a system is disclosed in U.S. Pat. No. 5,973,787. A suitable rotating analyzer system is shown in U.S. Pat. No. 5,608,526. See also, U.S. Pat. No. 6,278,519. All of the above patents are incorporated herein by reference.

In the illustrated embodiment, a pair of movable mirrors is provided for controlling the beam propagation. In a first position, the mirrors are located out of the beam path and allow the beam to travel along a first beam path. In a second position, both mirrors are located within the beam path and cause the beam to travel along the second beam path. The moveable mirrors are specifically configured to provide high position accuracy and repeatability for a large number of switching cycles.

In the preferred embodiment, stepper motors that have a hollow shaft are utilized to rotate and control the waveplates. The stepper motors are placed such that the beam paths run through the hollow shaft of the stepper motors' axes of revolution. The hollow shaft assembly reduces significantly the space otherwise occupied by the mechanism for driving the waveplates contributing to a reduced footprint of the optical assembly. As a result, the optical assembly fits into the apparatus despite the increased number of individual optical components.

The combination of single light source and single detector in combination with reduced travel range, multiple alternate focused beams, hollow shaft waveplate assembly and moving mirrors provides for an ellipsometry apparatus that has a footprint smaller than the travel envelope LE for a given wafer size.

As noted above, the subject invention allows periodic structures to be measured from a preferred direction while using a reduced motion stage. It should also be noted that this system allows any measurement area to be measured from any direction. While it is generally true that maximum information may be obtained when measuring a periodic structure when the beam is directed perpendicular to the line structure, additional information may be obtained from measurements where the beam is also directed parallel to the line structure or even at a 45 degree angle with respect thereto. In cases where the measured structure is rather simple, this information alone might even be sufficient. The subject invention allows measurements from any desired direction. Such measurements could be used individually or combined in a regression analysis to more fully characterize the structure.

DETAILED DESCRIPTION

Figure 1:
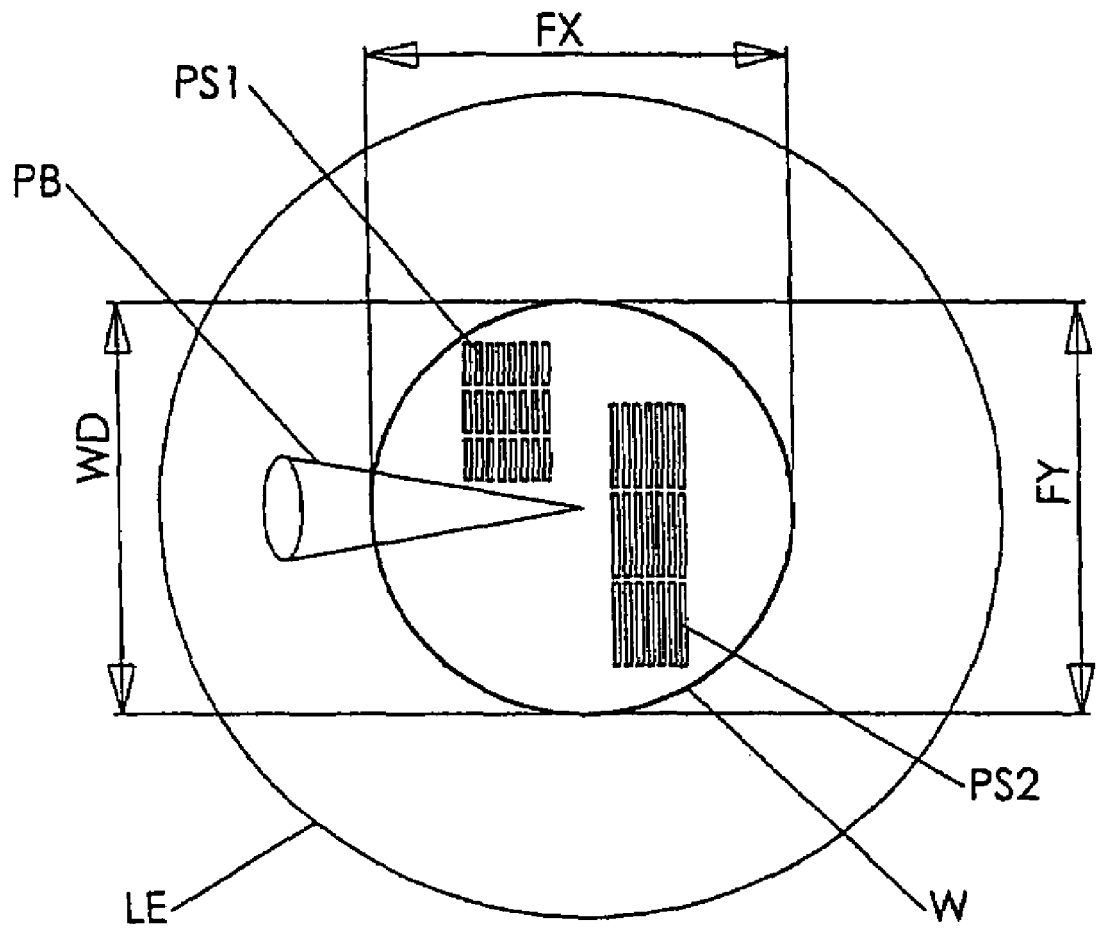
FIG. 1 shows a simplified scheme of a prior art positioning system of an ellipsometer system where two linear stages move a wafer in ranges about equal the wafer diameter.
Figure 2A:
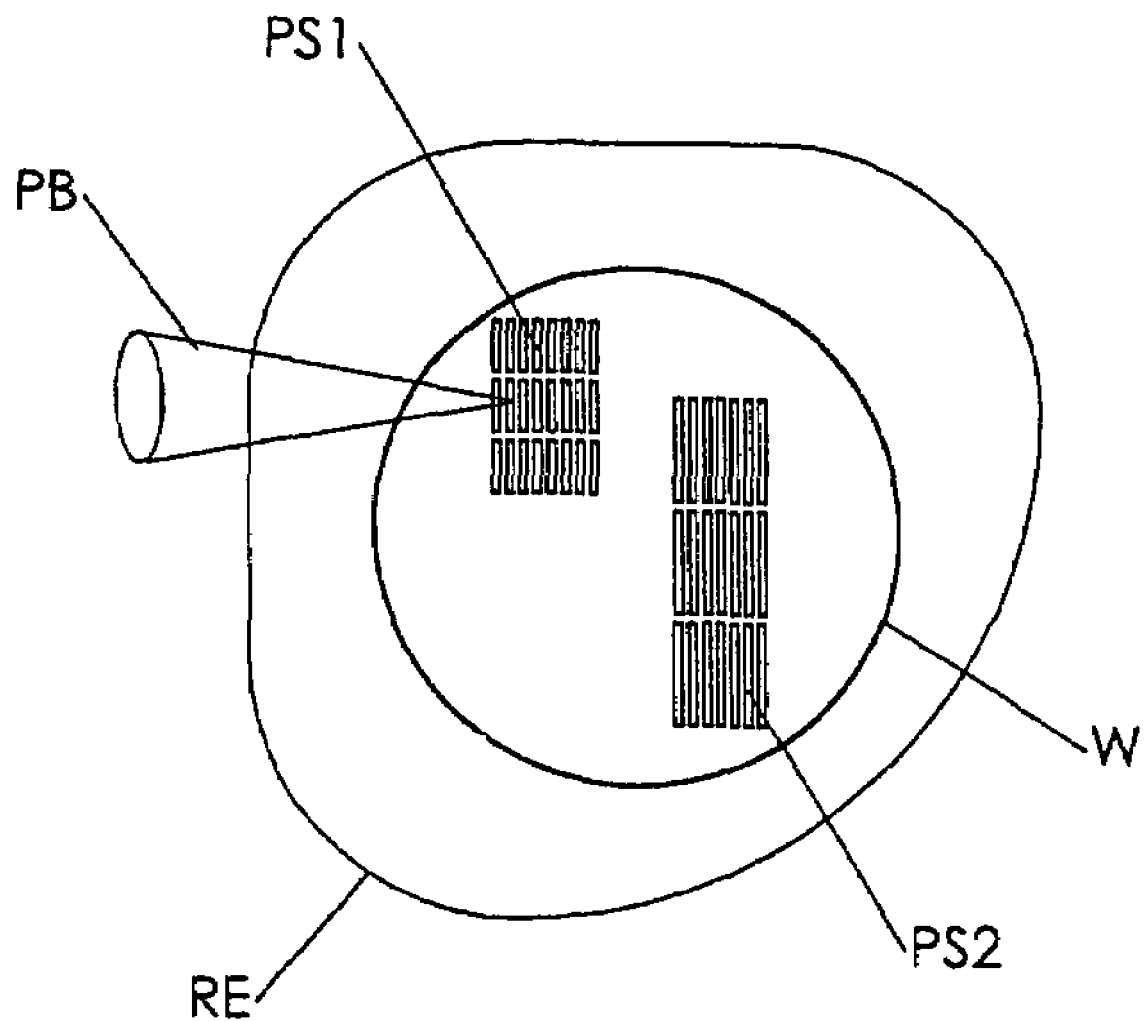
FIGS. 2A and 2B show simplified schemes of a prior art positioning system of an ellipsometer system where two linear stages move a wafer in ranges about half the wafer diameter. In such prior art positioning system the probe beam is limited to direction irrelevant reflectance measurements.
Figure 2B:
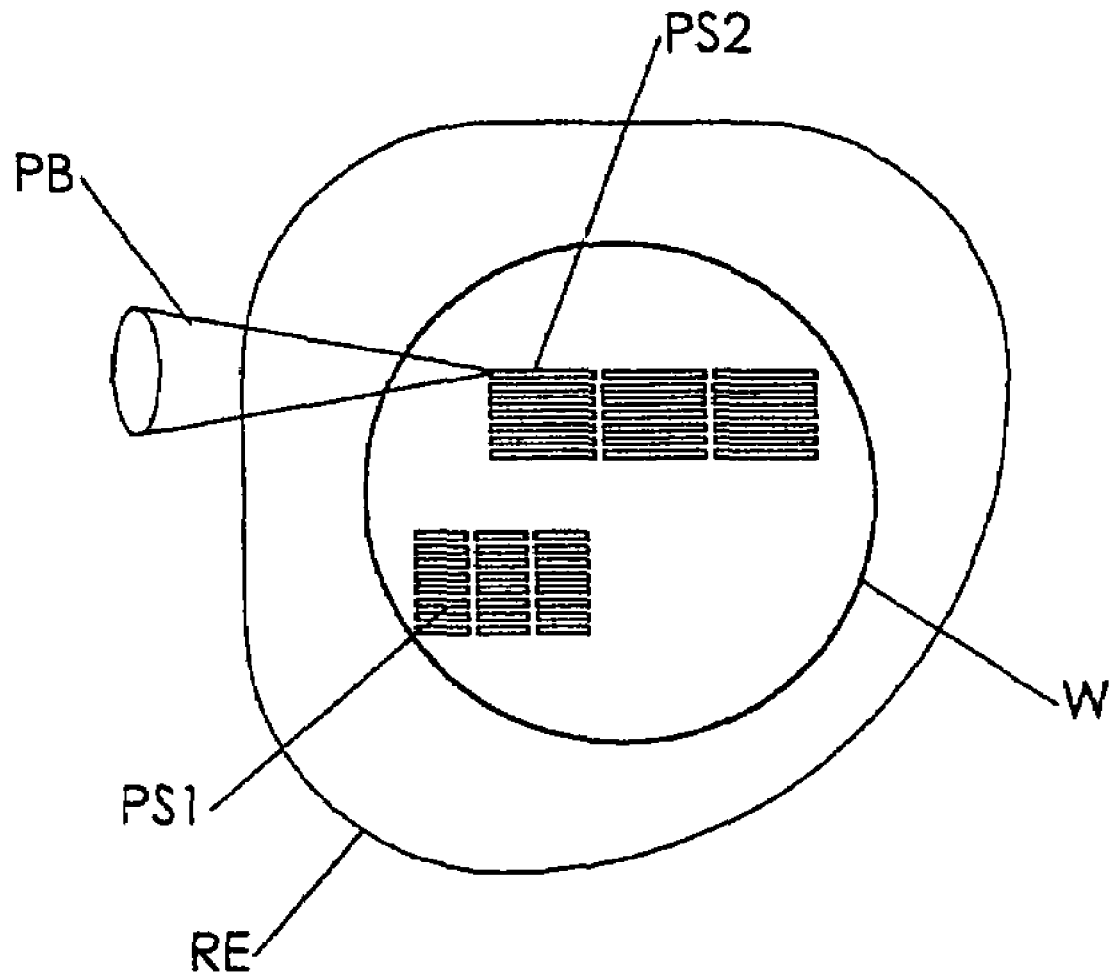
Figure 3:
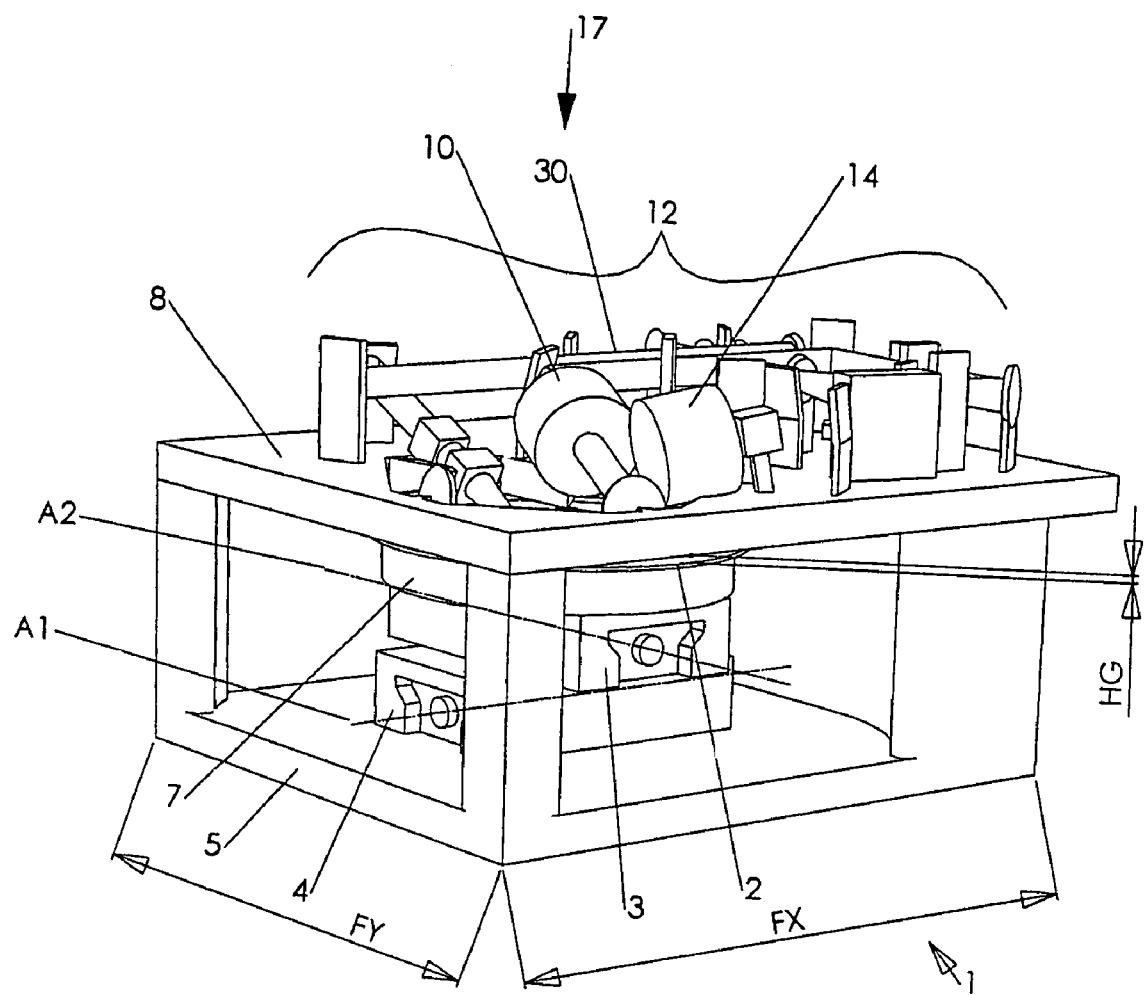
FIG. 3 shows a first perspective view of an exemplary apparatus according to the preferred embodiment of the present invention.

According to FIG. 3, an ellipsometric apparatus 1 of the preferred embodiment is configured in order to make directional reflectance (in this embodiment, ellipsometric) measurements on the top 9 (see FIGS. 4A, 5A, 6-10) of a wafer 2. The ellipsometric apparatus includes a base 5 and a top portion 8, which carries an optical assembly 12. The optical assembly 12 includes two rotating waveplate assemblies 10, 14.

Directional reflectance measurements are measurements for which a certain impinging direction of a focused beam relative to structure 6, 11 (see FIGS. 4A-10) needs to be maintained. The structures 6, 11 may be patterns as they are well known to those skilled in the art. The structures 6, 11 typically have a plurality of parallel lines in a grating-like configuration. The structures 6, 11 may also be layer configurations and other features on the wafer top 9 with properties measurable by the known techniques of ellipsometry. For more detailed information on related ellipsometry techniques, see the patents cited above.

It is noted that for the purpose of general understanding, the elements illustrated in the figures are schematically shown without any claim for accuracy. Moreover, for the purpose of clarity, propagating beams are shown as solids.

The ellipsometric apparatus 1 has a base 5 on which a first linear stage 4 is assembled. On top of the first stage 4 is mounted a second linear stage 3, which itself carries a rotating stage 7. The first stage 4 may have a first travel range TX (see FIG. 8) along a first linear axis A1 and the second stage 3 may have a second travel range TY (see FIG. 8) along a second linear axis A2 perpendicular to axis A1. First stage 4 and second stage 3 are positioned and computer controlled operated such that the rotating stage 7 may be moved within the apparatus as shown by a travel area TA (see FIGS. 8-10).

The travel area TA is defined by the ranges TX, TY. The travel area TA is the area accessibly by focal spots 41, 81 (see FIGS. 4A-7, 9, 10) by only operating the linear stages 3, 4. The travel area TA is a fictive and global entity introduced for the purpose general understanding. It can be imagined as being drawn by the focal spots 41, 81 on an fictive element directly attached to the linear stage 3 while the linear stages 3, 4 move within their travel ranges TX, TY.

Figure 8:
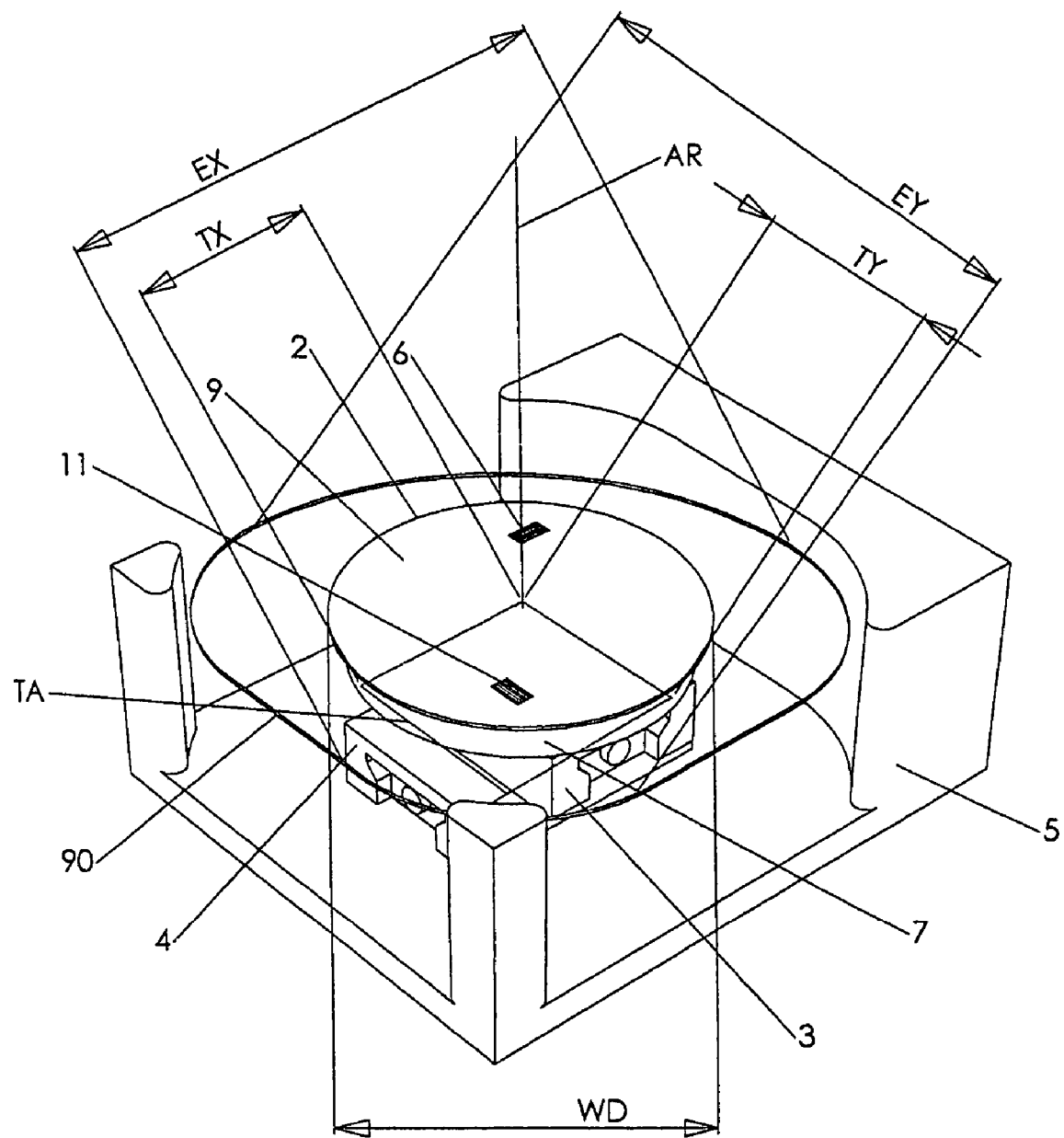
FIG. 8 shows the second perspective view with the device of FIG. 3 having a top portion removed. A travel envelope occupied by a work piece during the operational use of the device is illustrated. Also shown is a travel area provided by the travel ranges of the linear stages.
Figure 9:
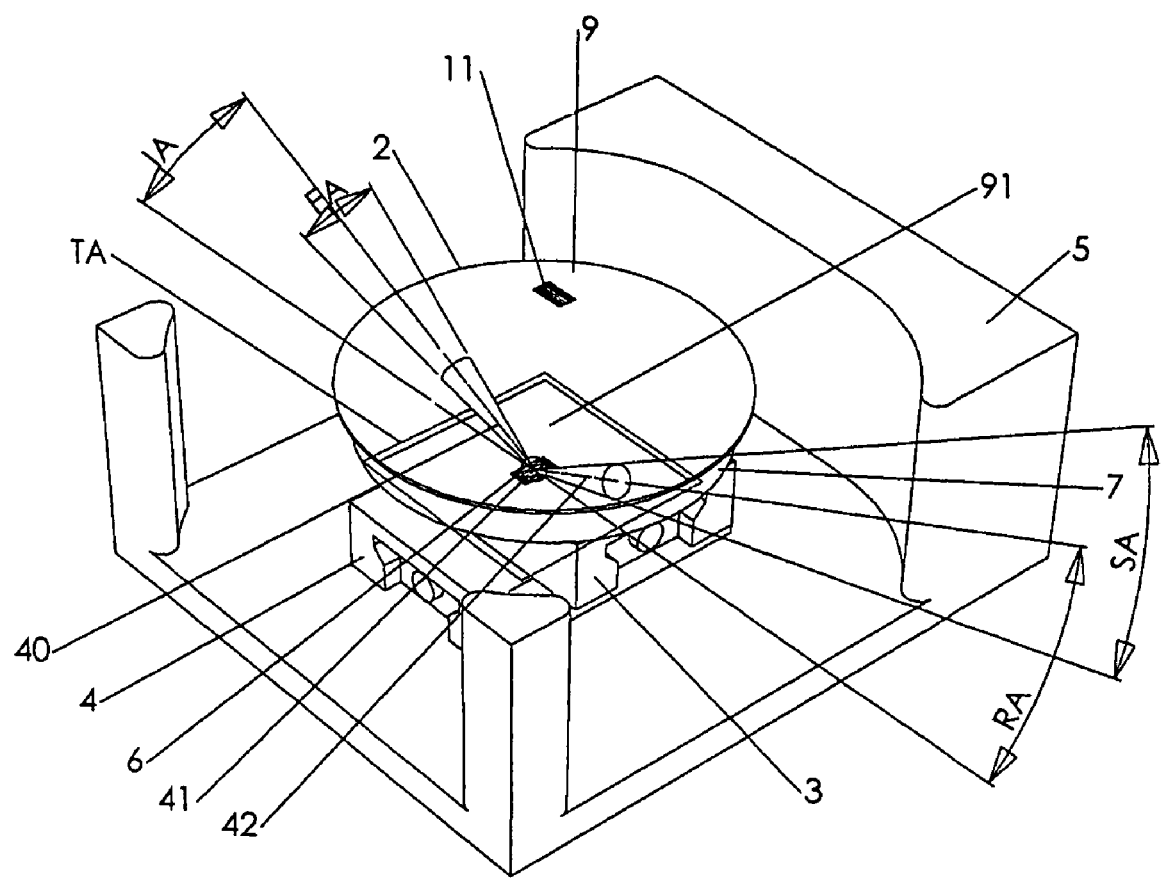
FIG. 9 shows the second perspective view with the device of FIG. 3 having the top portion removed. A first focused beam is illustrated impinging a first sensitive measurement area in a first impinging direction.
Figure 10:
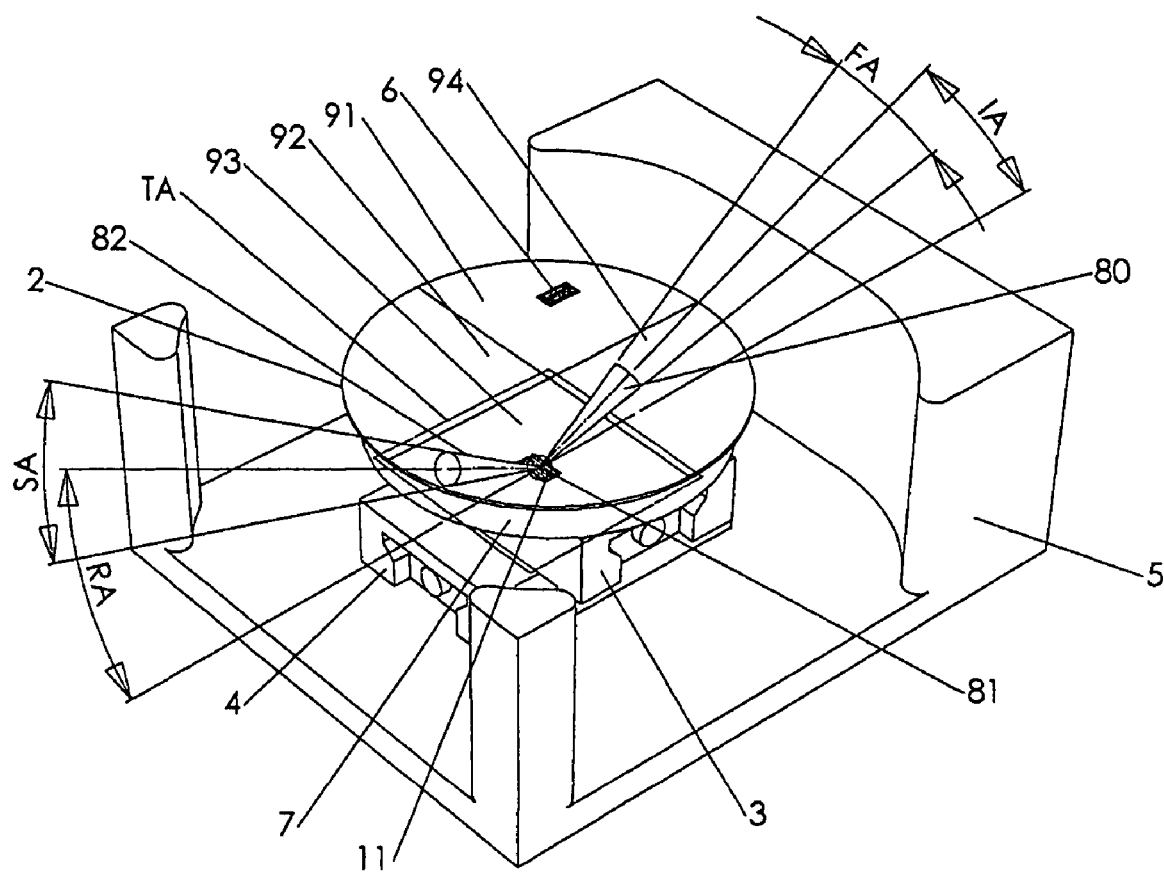
FIG. 10 shows the second perspective view with the device of FIG. 3 having the top portion removed. A second focused beam is illustrated impinging a second sensitive measurement area in a second impinging direction.

The rotating stage 7 has a rotating range preferably of 360 degrees around an axis of revolution AR (see FIG. 8). The rotating stage 7 is fixed on the linear stage 3 such that any area of the concentrically supported wafer 2 may be brought within the travel area TA by rotating the wafer 2 via the rotating stage 7.

In the preferred embodiment, the wafer 2 has a wafer diameter WD (see FIG. 8) that is about twice the amount of the ranges TX, TY. The first range TX defines together with the diameter WD a first envelope extension EX (see FIG. 8). The second range TY defines together with the diameter WD a second envelope extension EY (see FIG. 8). Extensions EX, EY define a travel envelope 90 (see FIG. 8).

Reflectance measurements are performed on essentially the whole wafer top 9 in a number of consecutive measurement steps where individual wafer sectors 91-94 (see FIGS. 9, 10) are brought within the travel area TA. Following the step of positioning one of the sectors 91-94 within the travel area TA, the wafer 2 is linearly moved by the stages 3, 4 to bring predetermined test areas within the focal spots 41, 81. The focal spots are fixed and defined by the optical assembly 12. A predetermined test area may be part of the structures 6, 11, which have different measurement relevant orientation on the wafer top 9. Structures 6, 11 are solely shown for the purpose of general understanding to exemplarily represent the dense arrayed patterns that are measured by the apparatus 1. The structures 6, 11 are direction sensitive measurement areas, which require a predetermined impinging direction in order to accomplish a reflectance measurement in accordance with known techniques of ellipsometry. A multitude of such direction sensitive measurement areas may be present on a wafer top 9 with varying angular fabrication orientation.

The apparatus top 8 is dimensioned in correspondence with the base 5 and may extend beyond the footprint of the base 5 for the purpose of providing secured access to supply and communication cables (not shown) as is clear to one skilled in the art. In the preferred embodiment, a common light source and a single final detector are utilized in order for the optical assembly 12 to fit within the apparatus top 8 together with eventual other functional elements like, for example a well known focusing unit and/or calibration unit (not shown). The apparatus top 8 is positioned in a gap height HG above the rotating stage 7 such that the rotating stage 7 is externally accessible for placing the wafer 2 on it.

In the preferred embodiment, the optical assembly 12 is configured to provide a first focused beam 40 (see FIGS. 3, 4A, 4B, 6, 9) and alternately a second focused beam 80 (see FIGS. 5A, 5B, 7, 10) from an initial light beam 30 (see FIGS. 3-7). The first focused beam 40 provides a first focal spot 41 in a first impinging direction (see FIG. 9). The second focused beam 80 provides a second focal spot 81 in a second impinging direction (see FIG. 10). Impinging directions are the directions of center axes of the focused beams 40, 80.

A first moveable mirror 28 (see FIGS. 4A-7) alternately switches the initial light beam 30 between a first beam path and second beam path. According to FIGS. 4A, 4B, the first beam path includes the initial section 31 up to a first lens unit 37 from which the first focused beam 40 propagates towards the first focal spot 41. The first beam path further includes a first inclining path segment 46 from a parabolic mirror 45 to the mirror 33 and a path end segment 50 from the mirror 33 up to a parabolic mirror 56.

Figure 5A:
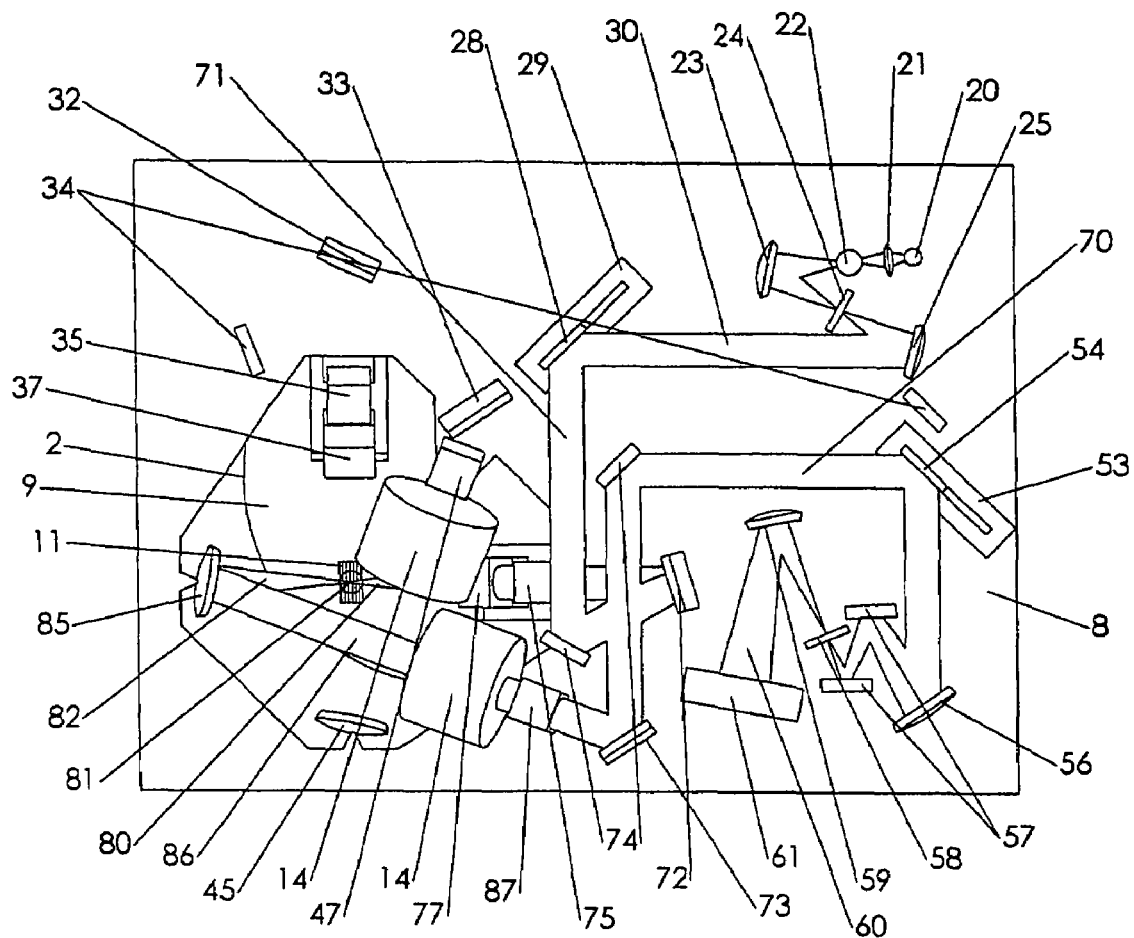
FIG. 5A shows a top view of the device of FIG. 3 as indicated in FIG. 3 by the arrow 17. The device is shown with the light beam propagating along a second beam path.
Figure 5B:
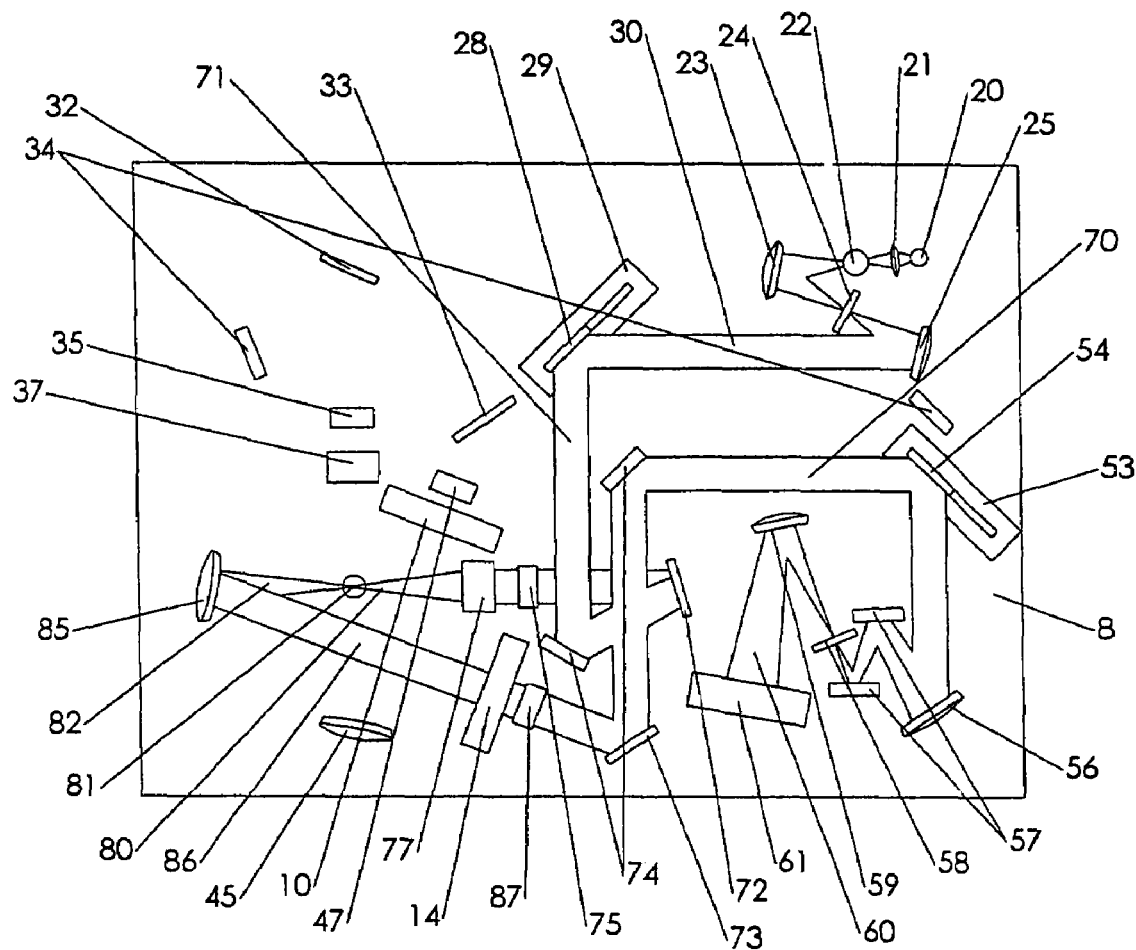
FIG. 5B shows schematic and simplified the main contents of FIG. 5A for the purpose of general understanding.

According to FIGS. 5A and 5B, the second beam path includes the initial section 71 from a first moveable mirror 28 being in an in-position such that it redirects the initial light beam 30 up to a second lens unit 77 from which the second focused beam 80 propagates towards the second focal spot 81. The second beam path further includes a second inclining path segment 86 from a parabolic mirror 85 to the mirror 73 and a path end segment 70 from the mirror 73 up to a second moveable mirror 54. The second moveable mirror 54 is also in an in-position where it redirects the incoming light beam towards the parabolic mirror 56. Light beams propagating along first or second beam path are both directed towards final optical elements, which prepare a terminating beam 60 to terminate on a single detector 61.

The final optical elements include the parabolic mirror 56 together with mirrors 57, a pin hole 58 and a holographic grating 59, which prepare in a well known fashion the terminating beam 60 for impinging and terminating in the final detector 61. In the preferred embodiment, the parabolic mirror 56 has a focus angle of 20° and a focal length of 100 mm, the holographic grating 59 is from Jobin Yvon, part number 543.02.190 and the final detector 61 is a CCD detector having 512 pixels, each corresponding to a different narrow wavelength bandwidth. The pin hole 58 includes a selectable element for changing the size of the pin hole so that the measurement spot size can be varied.

The scope of the invention includes embodiments in which other optical features well known for alternately redirecting an incoming light beam are used instead of the moveable mirrors 28, 54. The scope of the invention is also not limited by a specific mode by which the moveable mirrors 28, 54 alternately redirect the incoming beams. For example, a configuration may be selected in which one of the moveable mirrors 28, 54 is in an in-position while the other one is in an out-position where it does not interfere with a light beam. The scope of the invention is also not limited by a particular shape of geometry of the beam paths or by any particular number and/or configuration of additional optical elements like, for example, mirrors 34, 74.

Figure 4A:
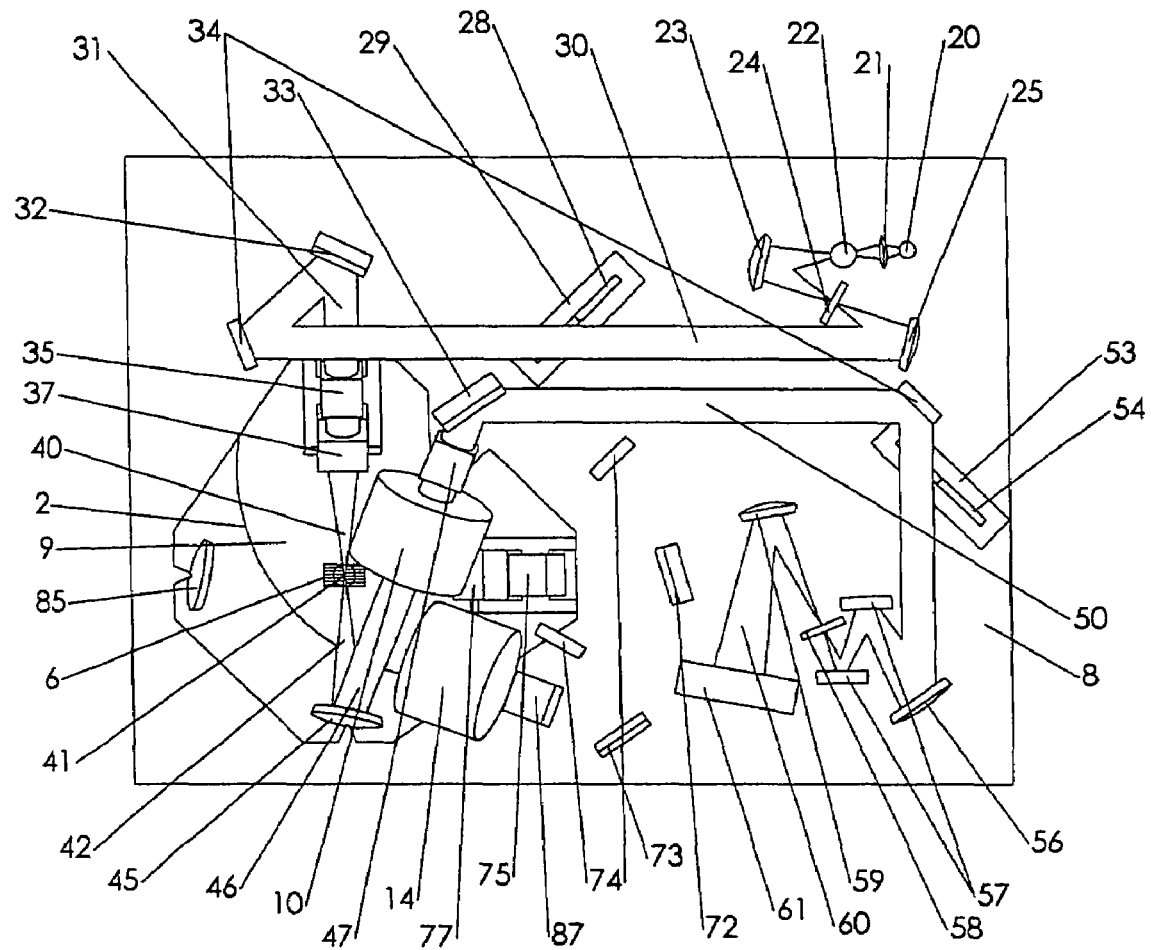
FIG. 4A shows a top view of the device of FIG. 3 as indicated in FIG. 3 by the arrow 17. The device is shown with a light beam propagating along a first beam path.
Figure 4B:
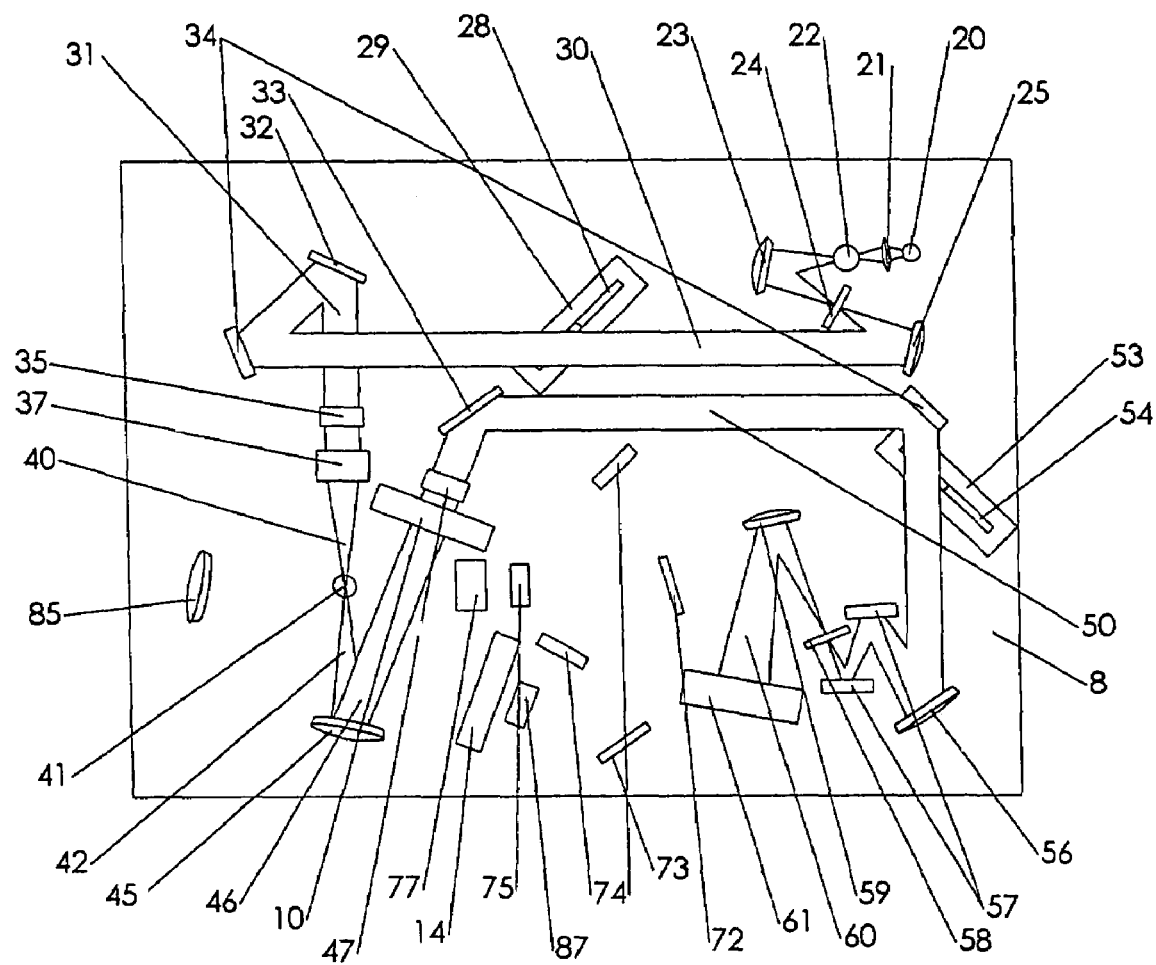
FIG. 4B shows schematic and simplified the main contents of FIG. 4A for the purpose of general understanding.

According to FIG. 4A, a first structure 6 has a measurement relevant orientation on the wafer top 9 requiring a first impinging direction provided by the first focused beam 40. In order to perform the reflectance measurement in accordance with the known techniques of ellipsometry, the first focused beam 40 impinges the structure 6 within the first focal spot 41 along the first impinging direction and initiates a first reflected beam 42 whose polarization state has been changed away from the focal spot 41. The first focused beam 40 is provided by a first lens unit 37 and a first polarizer 35, which focus and polarize the initial light beam 30 propagating along the first beam path. In the preferred embodiment, the first lens unit 37 is a triplet lens with f=69 mm and the polarizer 35 is a Rochon prism. A mirror 32 is spatially oriented to redirect the propagating beam from a horizontal beam plane towards the angulated oriented and lower positioned polarizer 35 and lens unit 37. The beam plane is sufficiently high above the top 8 to give room for mechanical features used, for example, for positioning and fixating the optical elements on the top 8.

The initial light beam 30 is provided by a light source, which may include but is not limited to a white light source 20, a lens 21, a UV light source 22, an ellipsoid mirror 23, a source pinhole 24 and a parabolic mirror 25. In the preferred embodiment, the white light source 20 is a tungsten light bulb, the UV light source 22 is a D2 UV-lamp, the ellipsoid mirror 23 has f=80 mm, and the parabolic mirror 25 has focus angle of 20° and f=50 mm.

To obtain an ellipsometric measurement with high accuracy, polarization detection needs to be performed on the reflected beams 42, 82 (see also FIGS. 7, 10) with only a minimum number of additional reflections induced on the reflected beams 42, 82. Since the reflected beams 42, 82 propagate conically away from the focal spots 41, 81, at least one optical element is used to collimate the reflected beams 42, 82. The collimating optic can be a lens, or as shown in the illustrated embodiment, parabolic mirrors 45, 85, which have in the preferred embodiment has a focus angle of 45° and f=59.51 mm.

In the present invention, polarization detection is performed by rotating the waveplate (under computer control) around an axis of revolution, which is parallel to the propagation direction of the beam passing through the waveplate with the beam centered on the rotation symmetry axis. In the present invention, the polarization detection is at a high level of accuracy by introducing two alternately operating rotating waveplate assemblies 10, 14 such that each of the two reflected beams 42 is passed through one of the two rotating waveplates with only a single prior reflection induced by the parabolic mirrors 45, 85. The waveplate assemblies 10, 14 include hollow shaft stepper motors with their rotor axes being collinear with a center axes of the reflected beams 42, 82, which propagate parallel along the inclining path segments 46, 86. The highly compact size of the waveplate assemblies 10, 14 accomplished by the use of hollow shaft stepper motors contributes significantly to the reduced space consumption of the optical assembly 12 and its successful integration into the apparatus 1 despite the increased number of optical components compared to that of a conventional apparatus having only a single focused beam.

Referring back to FIGS. 4A, 4B, a polarizer 47 is placed along each path segment after the first waveplate assembly 10. In the preferred embodiment, the polarizer 47 is a Rochon prism. The spatially oriented mirror 33 reflects the incoming beam and directs it along the first beam path within the horizontal beam plane.

According to FIG. 5A, a second structure 11 has an orientation on the wafer top 9 requiring a second impinging direction provided by the second focused beam 80. This orientation may be the result of the fact that the wafer is provided with structures having different measurement orientations in a single quadrant or the same measurement orientation in a neighboring quadrant. In the latter case, a structure with the same orientation on a neighboring quadrant of the wafer would need to be measured with the second SE path, since it would require a 90 degree stage rotation to get it into the area where it can be reached by the beam.

In order to perform the reflectance measurement, the second focused beam 80 impinges the second structure 11 within the second focal spot 81 along the second impinging direction and initiates a second reflected beam 82 that carries reflectance information away from the focal spot 81. The second focused beam 80 is provided by a second lens unit 77 and a second polarizer 75 that focus and polarize the initial light beam 30 propagating along the path section 71. In the preferred embodiment, the second lens unit 77 is similar to the first lens unit 37 and the second polarizer 75 is the similar to the first polarizer 35. A mirror 72 is spatially oriented to redirect the propagating beam from a horizontal beam plane towards the angulated oriented and lower positioned polarizer 75 and lens unit 77.

The second reflected beam 82 is reflected by the parabolic mirror 85 from which it propagates parallel along the second inclining path segment 86. A polarizer 87 is placed after the second waveplate assembly 14 along the path segment 86. In the preferred embodiment, polarizers 87, 47 are similar. A mirror 73 is spatially oriented to direct the incoming beam along the second beam path within the horizontal beam plane.

The second moveable mirror 54 is in an in-position where it interferes with the beam traveling along the end section

70. The second moveable mirror 54 reflects the beam again towards the parabolic mirror 56 and continues as described under FIG. 4A.

Figure 6:
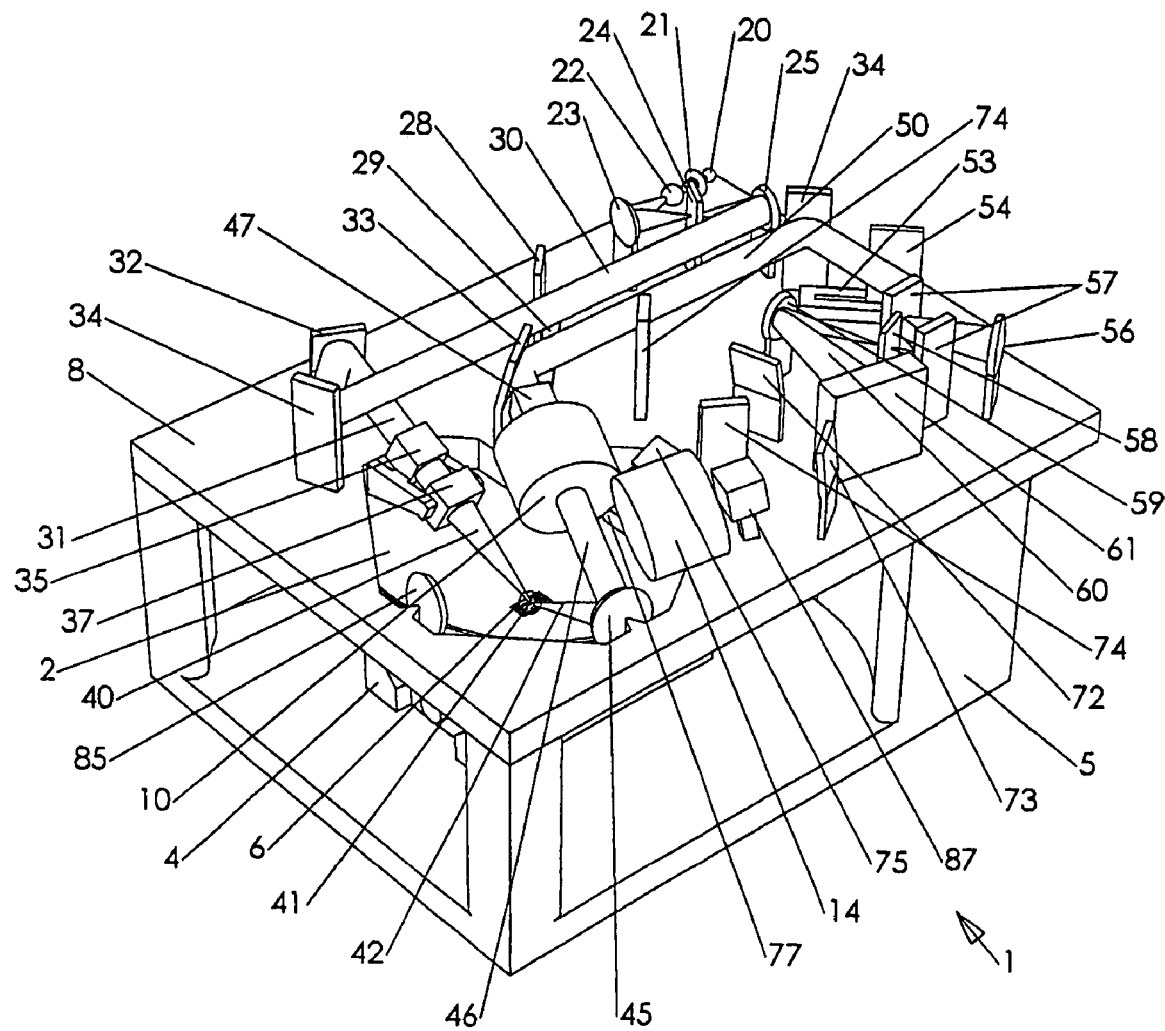
FIG. 6 shows a second perspective view of the device of FIG. 3 with the light beam propagating along the first beam path.
Figure 7:
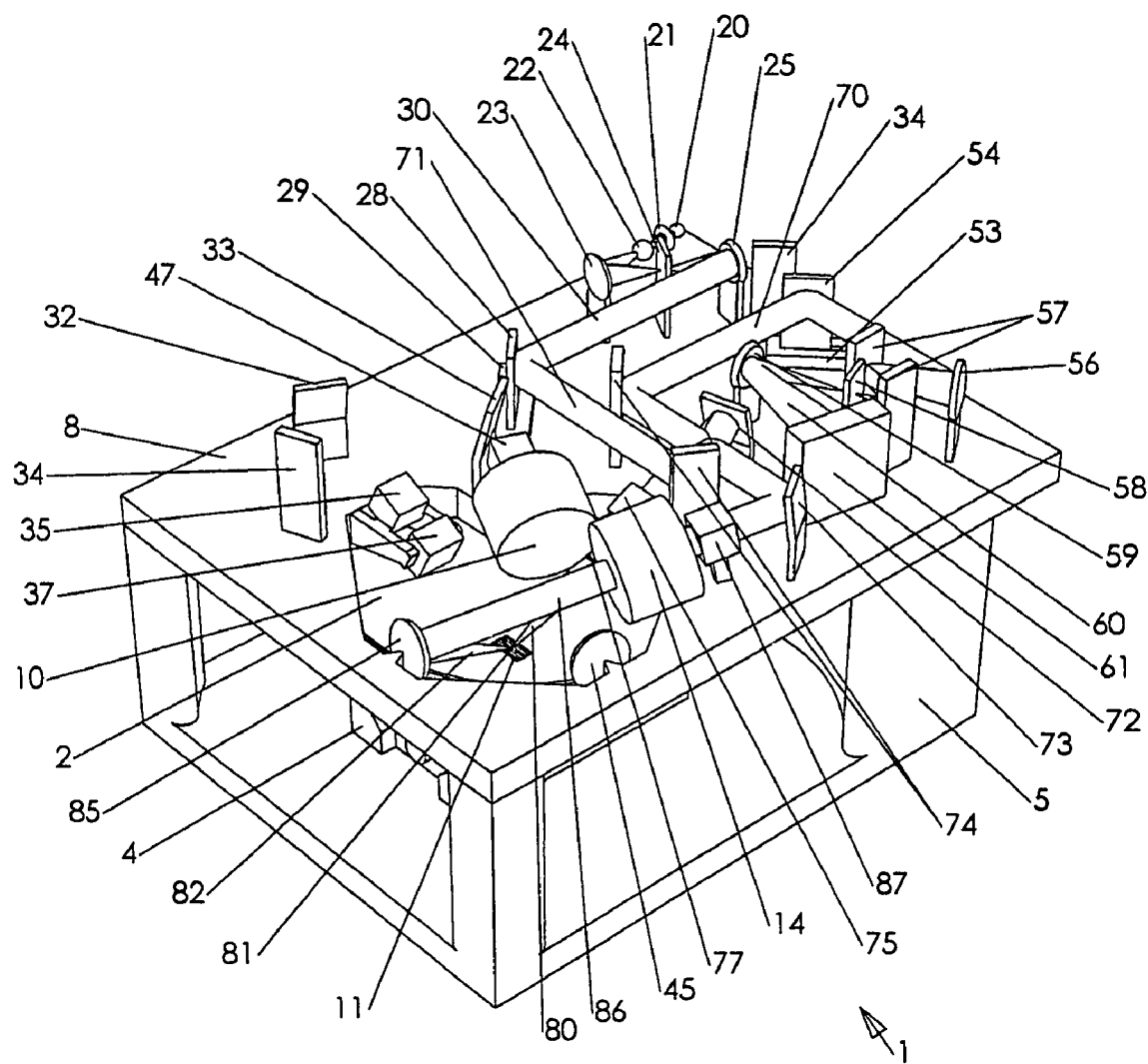
FIG. 7 shows the second perspective view of the device of FIG. 3 with the light beam propagating along the second beam path.

The perspective views of FIG. 6 and FIG. 7 illustrate the extent to which the compactness of the waveplate assemblies 10, 14 contribute to the small scale of the optical assembly 12 especially in the proximity of the focal spots 41, 81. For the purpose of clarity, FIG. 6 shows the first beam path and FIG. 7 shows the second beam path. FIG. 6 illustrates the limited space available for the waveplate assembly 14 between the path segment 46 and the polarizer 87. FIG. 7 illustrates the limited space available for the waveplate assembly 10 between the path segment 86 and the polarizer 47.

Referring to FIG. 8, the travel envelope 90 primarily defines the footprint of the apparatus 1 and consequently the available space on the apparatus top 8 as already explained in the above. Where the apparatus 1 is configured for measuring a wafer 2 having a diameter WD of about 300 mm, the envelope extensions EX, EY are according to the above description about 450 mm in each direction. The travel envelope 90 preferably remains within the overall boundaries of the apparatus 1 thus primarily defining a width FY (see FIG. 3) and a depth FX (see FIG. 3) of the apparatus 1. However to allow this instrument to be used in applications where smaller samples (e.g. 200 mm wafers) are used, while still requiring a minimal footprint, this instrument was designed minimizing the size of the optics plate 8 (FIG. 7) and allowing a 300 mm wafer to extend outside of the enclosure 5 (FIG. 7) in certain situations.

Other factors like, for example, structural requirements, additional space for cabling and other well known components of an ellipsometric apparatus are secondarily defining the footprint of the apparatus 1. Other well known components may be part of the base 5 and/or the top 8. Such components may be required, for example, for controlling, processing, calibrating and/or focusing during the operation of the apparatus 1. Some of these components, like for example, a focusing unit and or a calibration unit may be placed on the top 8, which may additionally reduce the space available for the optical assembly 12.

The sectors 91-94 (FIG. 10) are predetermined and fictive areas on the wafer 2, which can be accessed for measurement without rotating the wafer 2. In the preferred embodiment and in accordance with the preferred travel ranges TX, TY, the sectors 91-94 are about one quarter of the wafer 2. Hence, the wafer 2 has to be rotated four times in a case where all four sectors 91-94 are accessed for reflectance measurements.

Prior to performing a measurement, the wafer 2 is loaded on the rotating stage 7 by a wafer-loading tool like, for example, a robotic arm that holds the wafer 2 on its bottom surface via a vacuum fixture and releases the wafer 2 on the rotating stage 7. The gap height HG is selected to provide sufficient space for loading and unloading of the wafer 2 even when a pin lifter assembly is used to raise the wafer to allow the robot arm to slip underneath and pick up the wafer. Due to eventual loading inaccuracies or other limitations in the loading cycle, the wafer 2 is typically globally reoriented such that the orientation of the structures 6, 11 corresponds to impinging directions. The rotating stage 7 may be configured to perform such initial global orienting. In this regard, a flat or notch finding procedure may be performed followed by a mask alignment procedure using a pattern recognition system.

The optical geometry relevant in that context includes an angle of incidence IA and a focusing angle FA (see FIGS. 9, 10) of the focused beams 42, 82. In the preferred embodiment, the angle of incidence IA (in the Figures, defined with respect to the surface of the wafer) is about 25 degrees. The focusing angle FA or cone is between 1-6 degrees. The reflected beams 42, 82 have a corresponding reflecting angle RA and a spreading angle SA.

As illustrated in FIGS. 6, 7, the sizes and positions of the lens units 37, 77 and the parabolic mirrors 45, 85 are influenced by the angles IA, FA, RA, SA in combination with the gap height HG. Sizes and positions of the lens units 37, 77 and the parabolic mirrors 45, 85 again define the available space for dimensioning and positioning the waveplate assemblies 10, 14. The use of hollow shaft stepper motors significantly assists in down scaling the waveplate assemblies 10, 14 so that they are positioned along the inclining path segments 46, 86 without interfering with the lens units 37, 77.

The waveplates are mounted in the hollow portions of the rotor shafts, and are concentrically fabricated relative to the rotor axes. The absence of separate waveplate bearings and a mechanical transmission system greatly simplifies the design and provides at the same time for a more accurate rotation control of the waveplates. Since the rotor bearing of the stepper motor is also the bearing for the waveplates, specific bearing tolerances and tolerances for concentricity of the hollow portion of the rotor shaft are defined to meet the precision demands of optical assembly 12. In the preferred embodiment, linear actuator stepper motors from Eastern Air Devices were used.

Figure 11:
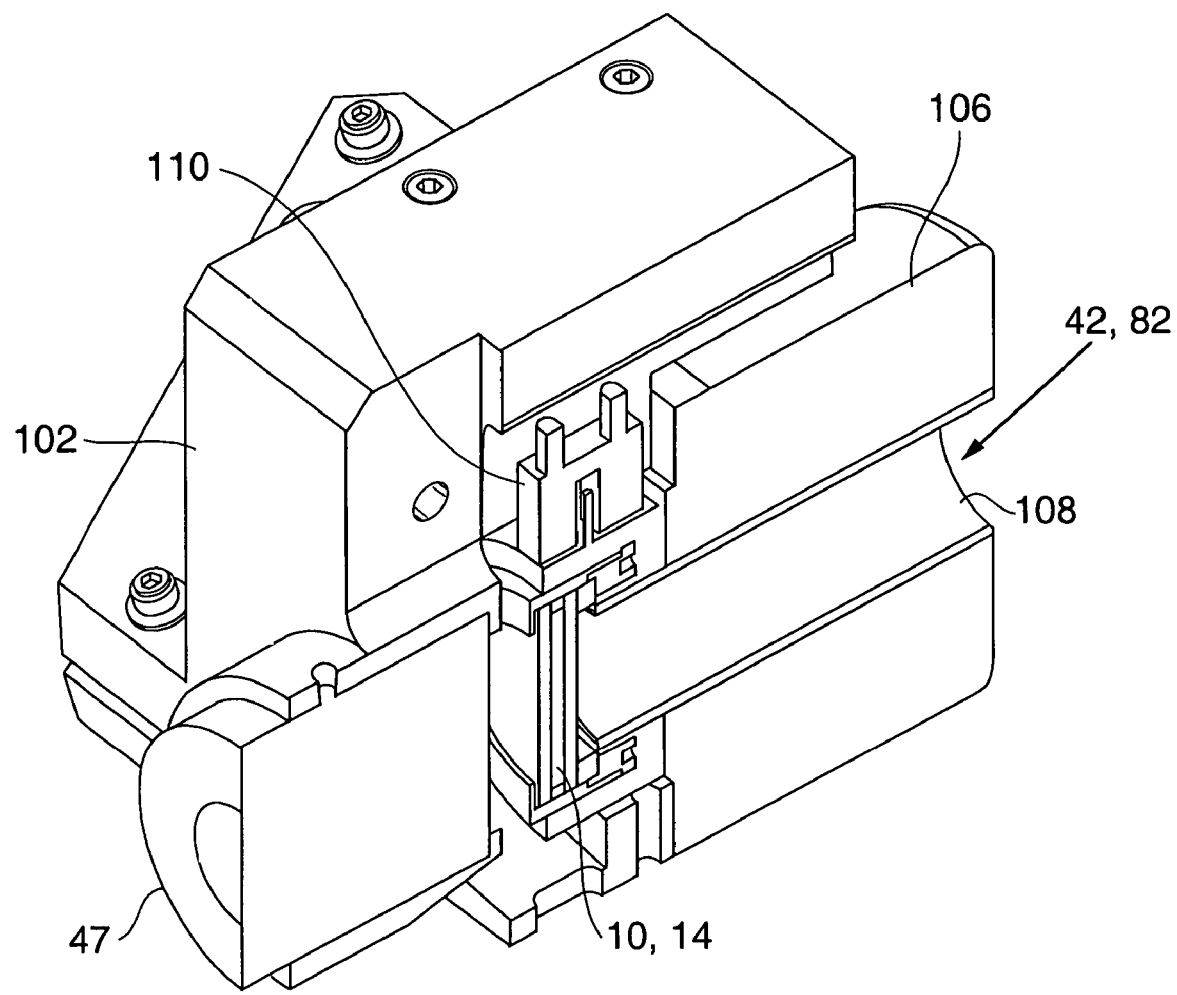
FIG. 11 is a perspective view of a hollow shaft stepper motor used to mount a rotating waveplate.

FIG. 11 illustrates the optical mount 102 for the waveplate. Mount 102 supports stepper motor 106 having a rotating hollow shaft 108 therein. The waveplate is mounted to the end of the shaft 108 and is carried thereby. Reflected probe beam light (42, 82) passes through the hollow shaft and waveplate and thereafter passes through the analyzer (polarizer) 47. The output of a home sensor 110 provides feedback for the position of the hollow shaft.

Another factor for keeping the size of the optical assembly 12 to a minimum is to utilize a common light source and a single final detector 61 as described above. In order to direct the initial light beam 30 and the reflected beams carrying the reflectance information, the moveable mirrors 28, 54 have to be switched into their in-position with highest accuracy over a high number of switching cycles. The movement and positioning of the moveable mirrors 28, 54 are provided by actuator units 29, 53. In the preferred embodiment, the actuator units 29, 53 linearly move the mirrors 28, 54. The actuator units 29, 53 are computer controlled and pneumatically operated. They provide custom designed hardened steel guides to achieve position precision over a large number of switching cycles. The precision requirements for the mirrors 28, 54 in their in-positions is 0.0050° angular tolerance for 1 million switching cycles.

A measurement of a wafer 2 within the inventive apparatus may be performed by the following steps. In a first step, the wafer 2 is loaded, fixated and eventual globally reoriented. In a second step, the first sector 91 is rotated and brought within the test area TA. Then, one of the first or second focused beams (40, 80) is activated to perform the desired measurements. Conceivably, all of the areas of interest within one sector could be measured by only one of the two beams. However, depending on the orientation of the structures and the type of measurement sought, it may be either necessary or desirable to use both beam (at different times) to measure all the features of interest in a given sector. For example, to gain further information about a periodic structure, two measurements might be made, one with beam 40 perpendicular to the periodic structure and a second with beam 80 parallel to the periodic structure.

Once the measurements of the first sector 91 are completed, the rotating stage 7 rotates the second sector 92 within the travel area TA so that measurements in this sector can be obtained. After all predetermined sectors 91-94 have been measured, the wafer 2 is unloaded from the apparatus 1.

The output from the detector 61 is supplied to a processor for analysis. The type of analysis performed is based on the type of measurement as is well known to those skilled in the art. For example, thin film parameters of a multi-layer structure can be characterized from multi-wavelength reflectometric or ellipsometric data using a theoretical model and the Fresnel equations. Information about small periodic structures (critical dimensions) can be derived using a diffraction model including, for example, rigorous coupled wave theory. (See U.S. Pat. Nos. 5,867,276 and 5,963,329, both incorporated herein by reference.)

The scope of the present invention includes embodiments, where the apparatus 1 is configured to make reflectance measurements on work pieces having features suitable to be measured with ellipsometric techniques as described in the above. Further more, the invention includes embodiments, where the work piece is non circular, and at least one of the ranges TX, TY is less than a parallel width of the fixed work piece.

In the preferred embodiment, two separate beam paths are provided within a single photodetector system as exemplarily illustrated by the final optical elements 56, 57, 58, 59 and the final detector 61. Nevertheless, the scope of the present invention includes embodiments in which two physically separate photodetector systems may be provided. In such embodiment, each of the two separate photodetector systems receives one of the two reflected beams 50, 70 thus further reducing the number of optical elements in the path of the reflected beams 50, 70. No moveable mirror 54 is present is such embodiments. Also, the scope of the present invention includes embodiments, where two separate light sources as exemplarily illustrated by the elements 20-25 are provided. In such embodiments, no moveable mirror 28 is present.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. An ellipsometer for evaluating characteristics of a semiconductor sample comprising:
    a broadband light source for generating a polychromatic probe beam;
    a first set of optics for selectively directing the probe beam to reflect off the sample at a non-normal angle of incidence and in a first direction;
    a second set of optics for selectively directing the probe beam to reflect off the sample at a non-normal angle of incidence and in a second direction different from the first direction;
    a detector system for selectively receiving the reflected probe beam from one of the first and second directions, said detector system for determining the change in polarization state of the beam induced by the sample and generating output signals in response thereto; and
    a processor for combining the output signals in a regression analysis to evaluate the characteristics of the sample.

2. An ellipsometer as recited in claim 1, wherein said broadband light source includes a first and second lamps with at least one of said lamps generating ultraviolet radiation.

3. An ellipsometer as recited in claim 1, wherein said detector system includes a grating and a CCD detector for generating output signals as a function of wavelength.

4. An ellipsometer as recited in claim 1, wherein the first direction is substantially perpendicular to the second direction.

5. An ellipsometer as recited in claim 1, wherein the detector system further includes a polarizing element and a retarding element positioned along the path of the probe beam.

6. An ellipsometer as recited in claim 5, wherein the retarding element is rotatable.

7. An ellipsometer as recited in claim 1, further including a stage means for moving the sample with respect to the probe beam, said stage means permitting both rotation and linear motion of the sample.

8. An ellipsometer as recited in claim 1, further including an optical element for selectively directing the probe beam into one of said first or second set of optics.

9. An ellipsometer as recited in claim 8, wherein said optical element is a movable mirror.

10. An ellipsometer as recited in claim 1, further including a movable mirror for selectively directing the beam to the detector system after reflection from the first and second directions.

* * * * *